United States Patent [19]

Corn

[11] Patent Number: 4,495,110

[45] Date of Patent: Jan. 22, 1985

[54] METHOD OF CONTINUOUSLY FORMING AN ACID FLUORIDE FROM CARBON MONOXIDE, ANHYDROUS HYDROGEN FLUORIDE AND AN OLEFIN

[75] Inventor: John E. Corn, Westerville, Ohio

[73] Assignee: Ashland Oil, Inc., Ashland, Ky.

[21] Appl. No.: 228,305

[22] Filed: Jan. 26, 1981

[51] Int. Cl.³ .............................................. C07C 51/58
[52] U.S. Cl. ................................................ 260/544 A
[58] Field of Search ........ 260/544 A, 544 F, 413 HC; 562/521

[56] References Cited

U.S. PATENT DOCUMENTS 2,831,877 4/1958 Koch .
2,876,241 3/1959 Koch .
3,059,005 10/1962 Van De Vusse et al. .
3,065,242 11/1962 Alderson et al. ................. 260/544 A
3,661,951 5/1972 Miller, Jr. et al. .
3,691,230 9/1972 Wesselingh ................. 260/413 HC

OTHER PUBLICATIONS

Perry, Robert H. et al., "Chemical Engineers' Handbook", 5th Ed. (1979), pp. 4–27 to 4–29, McGraw-Hill Publ.

*Primary Examiner*—Natalie Trousof
*Assistant Examiner*—L. Hendriksen
*Attorney, Agent, or Firm*—Wood, Herron & Evans

[57] ABSTRACT

A method of continuously forming an acid fluoride from CO, HF and an olefin comprising continuously mixing all of the reactants in an area of high turbulence and continuously transferring the mixed reactants from the area of high turbulence into a continuous reactor where most of the reaction takes place. This enables the reactants to be inexpensively combined and yet prevents the formation of a prohibitive amount of heat from this exothermic reaction.

4 Claims, 1 Drawing Figure

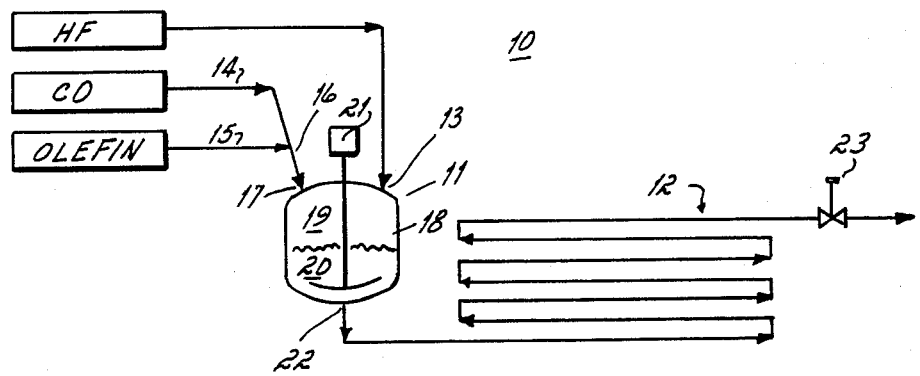

METHOD OF CONTINUOUSLY FORMING AN ACID FLUORIDE FROM CARBON MONOXIDE, ANHYDROUS HYDROGEN FLUORIDE AND AN OLEFIN

BACKGROUND OF THE INVENTION

The present invention relates to a method for forming acid fluorides from olefins, carbon monoxide and anhydrous hydrogen fluoride. Specifically the present invention relates to a method of continuously forming an acid fluoride using anhydrous hydrogen fluoride an olefin and carbon monoxide wherein the polymerization and dimerization of the olefin is minimized and provision is made for the removal of heat created in the reaction.

Much of the art used in the production of acid fluorides actually relates to the production of carboxylic acids. Acid fluorides are typically produced by reacting carbon monoxide, an olefin and anhydrous hydrogen fluoride. This is disclosed in Koch U.S. Pat. No. 2,831,877. Typically the reaction is continued and water is added to the acid fluoride to form hydrofluoric acid and carboxylic acid. The present invention deals with the formation of the acid fluoride and is not necessarily directed to the formation of the carboxylic acid. However, the preferred embodiment of the present invention includes a hydrolysis step whereby the acid fluoride is reacted with water to form a carboxylic acid.

There are two major problems associated with the formation of acid fluorides. The first is the heat formed during the reaction. Since this is an exothermic reaction, there can be a great deal of difficulty with carrying away the reaction heat. This does not present a significant problem if the size of the reactor is so small that the reactor vessel can absorb the heat without being damaged and without the heat of the reactants exceeding the maximum permissable temperature. However, in larger reactors there is a significant problem with the formation of heat. This problem can typically be eliminated by use of a continuous reactor such as a plug-flow reactor in which the reactants are pumped through a tube which is surrounded with a water jacket or some other cooling process. The tube provides sufficient residence time to allow the reagents to react and provides a large amount of surface area to transfer the heat away from the reaction.

The second problem encountered during the formation of the acid fluorides is the dimerization of polymerization of the olefins used in the reaction. A typical means to avoid this problem in the past has been to constantly agitate the reagents to sufficiently disperse the olefin so that no localized area of high concentration of olefin occurs. A further means to prevent these side reactions is to maintain a sufficient concentration of CO in solution. This can also be accomplished by continuously mixing the reactants so that gaseous CO is constantly dispersed in the liquid HF and olefin mixture. Thus, as the CO which dissolved in the liquid is reacted, the dispersed CO readily dissolves and is available to react with the olefin. This is easily accomplished in a batch type reactor where a constant stirring can be economically achieved. Unfortunately, as stated above, the batch reactor presents the problem of cooling efficiency.

One possible method of overcoming these problems is to incorporate an in-line mixer with a tubular reactor wherein the hydrogen fluoride and carbon monoxide are mixed and forced into a tubular reactor. The olefin can then be admitted into the tubular reactor. The olefin can then be admitted into the tubular reactor at a plurality of injection points along the tubular reactor so that all of the olefin is not dispersed at once and the mixing requirements are minimized. In this manner, the turbulence created simply by the fluid flowing through the reactor is sufficient to maintain the olefin in the dispersed state, and more time is provided for the CO to disperse and dissolve in the liquid. However, this is costly and less efficient than the present invention.

Thus, according to the present invention, an olefin, CO and anhydrous hydrogen fluoride can be violently mixed together in one vessel referred to as an area of high turbulence and continuously injected into a tubular reactor where they form an acid fluoride. The tubular reactor does not require additional mixing vessels nor does the olefin need to be injected at various locations along the reactor.

This is particularly significant if the reactor is a tube bundle reactor with hundreds or even thousands of individual tubes. This invention discloses a method of overcoming these problems, yet allows the mass manufacture required to economically produce the acid fluorides and the carboxylic acids from the acid fluoride. The present reactor combines the stirring features of a batch reactor with the cooling abilities of a continuous flow tubular reactor.

BRIEF DESCRIPTION OF THE DRAWING

The FIGURE is a schematic diagram of the method of the present invention.

DETAILED DESCRIPTION OF THE INVENTION

The reagents used in the formation of the acid fluoride according to the present invention are anhydrous hydrogen fluoride, an olefin and carbon monoxide. This reaction is a dual phase reaction. The first, or gas, phase comprises CO. The second phase is a liquid phase comprising HF, the olefin, and CO which has dissolved in the liquid. Preferably, the liquid phase also includes dispersed gaseous CO.

The olefins suitable for the present invention include ethene, propene, butene, isobutene or higher molecular weight olefins such as nonene, hexadecene and the like, and mixtures thereof. The reaction can also be applied to cyclic olefins such as cyclohexene, and also to diolefins as for example, butadiene and 4-vinyl cyclohexene-1 and in general, to olefinic compounds such as unsaturated carboxylic acids, for example, oleic acid. Difficulty may be incurred when using higher molecular weight olefins due to their viscosity. It is preferable to use $C_3$–$C_{12}$ olefins.

The hydrogen fluoride used in the present invention must be in the anhydrous state or the reaction will form a carboxylic acid instead of an acid fluoride. In addition, anhydrous hydrogen fluoride is preferred even when a carboxylic acid is the desired end product since anhydrous hydrogen fluoride is substantially less corrosive than an aqueous solution of hydrogen fluoride.

The molar ratio of olefin to carbon monoxide to hydrogen fluoride in the present invention should be about 1:1–3:5–100, and preferably, about 1:1.10:14. In the present invention, the hydrogen fluoride acts not only as a reagent, but also as a solvent. The carbon monoxide is preferably added at least in slight excess to insure availability of carbon monoxide to olefin.

The reaction conditions are generally at elevated temperatures and elevated pressures. The temperature of the present reaction in the tubular reactor is generally up to about 90° C. and preferably, about 60° C. The pressure can vary between 500 to 5000 psig and typically, the reaction is run at approximately 2800 psig.

A reactor useful in the present invention is schematically depicted in the FIGURE. The reaction system 10 includes a mixing vessel 11 and a continuous reactor 12.

The mixing vessel is an autoclave connected to sources of anhydrous hydrogen fluoride, carbon monoxide and an olefin. The HF is injected into the autoclave at point 13 and the CO and olefin travel through lines 14 and 15 respectively, which merge into a common tube 16 which leads to a second injection point 17. The autoclave is maintained at at least the reaction pressure.

The reactants, i.e., HF, CO and olefin, are continuously injected into the autoclave wherein the olefin and HF mix. CO dissolves as well as disperses in this HF-olefin mixture. As shown in the FIGURE, the area 18 within the autoclave includes a gas phase 19 comprising CO and a liquid phase 20 comprising HF and olefin and dissolved and dispersed CO. The liquid phase is constantly being maintained in a state of high turbulence by means such as a stirrer 21.

This liquid phase containing dispersed CO is the area of high turbulence.

The bottom of the autoclave includes a dispensing port 22 which is in communication with the continuous reactor 12. This reactor should preferably include a cooling means such as a water jacket which is not shown. The interior of the continuous reactor 12 defines a volume which is the reaction zone. It is preferable that the reaction takes place in this zone so that the heat of reaction can be easily transferred away from the reactants.

The continuous reactor includes a valve 23 through which the product of the present invention exits. This could be a let down valve if it is desired to release the internal pressure.

The power required of the stirrer 21 will vary according to the size of the reactor as well as the operating temperature of the reactor, the flow rate within the tubular section of the reactor and reactor pressures. The quicker the reaction occurs, the more turbulent the dispersion must be since the CO in solution with HF will be depleted more quickly. Increased pressure may be desired to maintain more carbon monoxide in solution as well as for the purpose of forcing the reagents through the reactor more quickly. Furthermore, each of these variables will change according to the olefin used. Therefore, the strength of the mixer must be determined by the individual operator of the reactor considering operating conditions. It is maintained that one of ordinary skill in the art using the teachings of the present invention can arrive at such decision.

The size of the high turbulent mixing area is extremely significant with respect to the present invention. The larger the area, the more heat will be generated and the less likely it will be that the reactants will be completely mixed. Therefore, the high turbulence area should be maintained sufficiently small so that the reactants do not completely react within the mixing vessel and the heat formed during the reaction is not so substantial as to cause damage to the mixing vessel.

The continuous reactor preferably is a tube reactor and for the purpose of mass production, would be a tube-bundle reactor in which hundreds or thousands of tubes are combined in the same reactor. The purpose of the tube reactor is to give sufficient residence time for the reagents to completely react and to provide a heat transfer surface so that the reaction temperature can be maintained within permissible limits. The length of the reactor tube will depend substantially on the flow rate, reaction temperature, and the olefin which is being reacted. The reaction should be conducted at a sufficiently fast rate that additional mixing is not required to maintain the CO in a dispersed state and available to react with the olefin. Generally, this dispersion can be maintained for about 300 seconds.

In operation, HF, CO and the olefin are continuously injected into the autoclave, thereby forming a liquid phase and a gas phase. The liquid phase is constantly maintained in a highly turbulent state and the gas phase is constantly being dispersed within the liquid phase by means such as a stirrer. This matter comprising the liquid phase continuously passes from the autoclave into the continuous reactor.

While passing through the continuous reactor, the HF, CO, and olefin react to produce an acid fluoride. This acid fluoride as well as excess HF and any excess CO are continuously released from the reactor at valve 23.

The period during which the reagents remain in the area of high turbulence is critical and must be minimized. In any event, this must not be long enough for the reagents to produce a prohibitive amount of heat.

Prohibitive amount of heat in the present invention is that amount of heat which would cause the temperature of the reagents in the high turbulence area to exceed about 90° C. At 100° C., the formation of the acid fluoride significantly decreases in favor of the polymerization or dimerization of the olefin. Therefore, the temperature must be maintained below 100° C. and preferably, below 90° C.

The heat within the area of high turbulence will naturally tend to be transferred to the environment. In addition, some cooling means can be used to assist this heat transfer. But the basic method of the present invention is to transfer the reagents from the area of high turbulence to the continuous reactor before a prohibitive amount of heat is generated. Generally, this is accomplished by maintaining the volume of the area of high turbulence small. Since this is a continuous process, the reagents are continuously fed into the area of high turbulence and continuously flow out of this area. Therefore, the smaller this high turbulent area is, the less time the reagents will be in the mixer and the less time reactants will be generating heat within the high turbulence area.

The high turbulence area can be generally defined with respect to the time the reactants are in the mixer. The area of high turbulence should not be so large that the reactants remain in this area more than about 1/10th of the total reaction time. Generally, the reaction time will be between 10 to 300 seconds depending on reaction conditions. The reaction time for particular conditions can be empirically determined by conducting the reaction under desired conditions and continuously monitoring the presence of olefin. Based on this, the reagents should pass through the area of high turbulence within 1 to 30 seconds.

The area of high turbulence can also be defined with respect to the volume of the reaction zone. The reaction zone is defined as the volume of that portion of the continuous reactor in which the formation of acid fluoride occurs. Basically, the reaction is occurring until all of the olefin is consumed. Therefore, the actual volume of the reaction zone can be determined by monitoring the olefin at various points along the tubular reactor. As soon as no more olefin is present, the reaction zone has been passed. The volume of the high turbulence area should not exceed about 1/10th of the reaction zone.

However, the most critical means to determine if the area of high turbulence is small enough is the temperature. As long as this is less than 90° C., the area is sufficiently small.

The acid fluoride formed by the present invention can be further reacted with water to form a carboxylic acid and hydrogen fluoride. The carboxylic acid can then be removed and the hydrogen fluoride recycled back into the turbulent mixer.

EXAMPLE

The following example is presented as a means to further educate one of ordinary skill in the art with respect to the means to carry out the present invention. The reactor used in the present example comprised two components, a high turbulence mixer and a continuous tubular reactor. The high turbulence mixer comprised a 1 liter autoclave which is only 20% filled with liquid. Therefore, the area of high turbulence is 0.2 liter. The mixer includes two inlets positioned above the container and 1 outlet at the bottom of the container which was connected directly to the second stage tubular reaction portion of the reactor. The high turbulent area included a 0.5 horsepower mixer. The tubular reactor comprised a ½ inch diameter tube 40 feet in length which was cooled by means of a water jacket.

The reaction was conducted using propene as an olefin with the molar ratio of olefin to carbon monoxide to hydrogen fluoride being 1:1.5:15. The reaction was conducted at 30° C. with a flow rate of 2.4 lb/hr and a pressure of 2800 psig at the inlet.

The reagents were injected into the autoclave at the following rates:

HF—4290 g/hr,
CO—8 l/min (600 g/hr),
Propene—600 g/hr.

The propene was 100% reacted with a selectivity to isobutyryl fluoride of 90%.

This indicates that the present invention does in fact present a means to continuously produce an acid fluoride without expensive in-line mixers or cooling means and enables one to economically continuously produce acid fluorides from CO, HF and olefin without causing excessive polymerization or dimerization of the olefin.

Having thus described the invention, I claim:

1. A method of continuously forming an acid fluoride from anhydrous hydrogen fluoride, carbon monoxide, and an olefin comprising
    (a) continuously injecting the anhydrous hydrogen fluoride, carbon monoxide, and olefin into an area of high turbulence to form a reactant mixture;
    (b) continuously transferring the reactant mixture from the area of high turbulence to a continuous reactor
   wherein the temperature of the reactant mixture within said area of high turbulence is maintained at about 90° C. or less.

2. The method as claimed in claim 1 wherein the temperature of the reactant mixture within said area of high turbulence is maintained at about 90° C. or less by controlling the time the reactant mixture remains in the area of high turbulence.

3. The method as claimed in claim 2 wherein a reaction time is defined as the time required for the reactant mixture to completely react and wherein the time the reactant mixture remains in the area of high turbulence does not exceed 1/10 the reaction time.

4. The method of forming an acid fluoride as claimed in claim 1 wherein a reaction zone is defined, said reaction zone comprising the volume of that portion of the continuous reactor in which any unreacted olefin is present;
    wherein the temperature of the area of high turbulence is maintained below 90° C. by maintaining the area of high turbulence at less than 1/10 the volume of the reaction zone.

* * * * *